US012642877B2

(12) United States Patent
Yang et al.

(10) Patent No.: US 12,642,877 B2
(45) Date of Patent: Jun. 2, 2026

(54) PROBE STERILIZATION DEVICE, PROBE STERILIZATION METHOD, AND ULTRASONIC IMAGING SYSTEM

(71) Applicant: GE Precision Healthcare LLC, Wauwatosa, WI (US)

(72) Inventors: Yalan Yang, Wuxi (CN); Lionel Wodecki, Buc (FR); Yang Zhou, Wuxi (CN); Bo Dan, Wuxi (CN); Hao Yin, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 870 days.

(21) Appl. No.: 17/869,447

(22) Filed: Jul. 20, 2022

(65) Prior Publication Data

US 2023/0033190 A1 Feb. 2, 2023

(30) Foreign Application Priority Data

Jul. 30, 2021 (CN) .......................... 202110872476.4

(51) Int. Cl.
A61L 2/10 (2026.01)
A61B 8/00 (2006.01)

(52) U.S. Cl.
CPC .............. A61L 2/10 (2013.01); A61B 8/4422 (2013.01); A61B 8/4433 (2013.01); *A61L 2202/122* (2013.01); *A61L 2202/14* (2013.01)

(58) Field of Classification Search
CPC ........ A61L 2/10; A61L 2/18; A61L 2202/122; A61L 2202/24; A61B 8/4422; A61B 8/4433
See application file for complete search history.

(56) References Cited

U.S. PATENT DOCUMENTS

| | | | | |
|---|---|---|---|---|
| 6,781,287 B1* | 8/2004 | Dam | ................... | G01F 23/2968 |
| | | | | 310/334 |
| 2014/0241942 A1* | 8/2014 | Coles | ...................... | A61L 2/186 |
| | | | | 422/36 |
| 2016/0324997 A1* | 11/2016 | Dayton | ...................... | A61L 2/10 |
| 2017/0296142 A1* | 10/2017 | Wodecki | .............. | A61B 8/4433 |
| 2019/0111202 A1* | 4/2019 | Falkovich | ............. | A61M 5/162 |
| 2020/0016285 A1* | 1/2020 | Newsome | ................. | A61L 2/26 |

FOREIGN PATENT DOCUMENTS

| | | | | | |
|---|---|---|---|---|---|
| CN | 105606210 A | * | 5/2016 | ............. | G01S 15/89 |
| CN | 107233594 A | * | 10/2017 | ............... | A61L 9/14 |
| JP | 2012196303 A | * | 10/2012 | ........... | A61B 8/4209 |

* cited by examiner

*Primary Examiner* — Maris R Kessel
*Assistant Examiner* — Eric Talbert
(74) *Attorney, Agent, or Firm* — SPQ IP LLC

(57) ABSTRACT

A probe sterilization device is provided. The probe sterilization device including: a housing defining a cavity with an opening, the housing including a cover plate capable of covering the opening; a cover plate drive, capable of driving, in response to a cover plate drive control signal, the cover plate to move so as to open the opening; a support, arranged in the housing and capable of fixing the probe; an ultraviolet light source, arranged in the housing and capable of being turned on in response to a light source control signal; and a processor, electrically connected to the cover plate drive and capable of sending the cover plate drive control signal to the cover plate drive, and electrically connected to the ultraviolet light source and capable of sending the light source control signal to the ultraviolet light source.

15 Claims, 6 Drawing Sheets

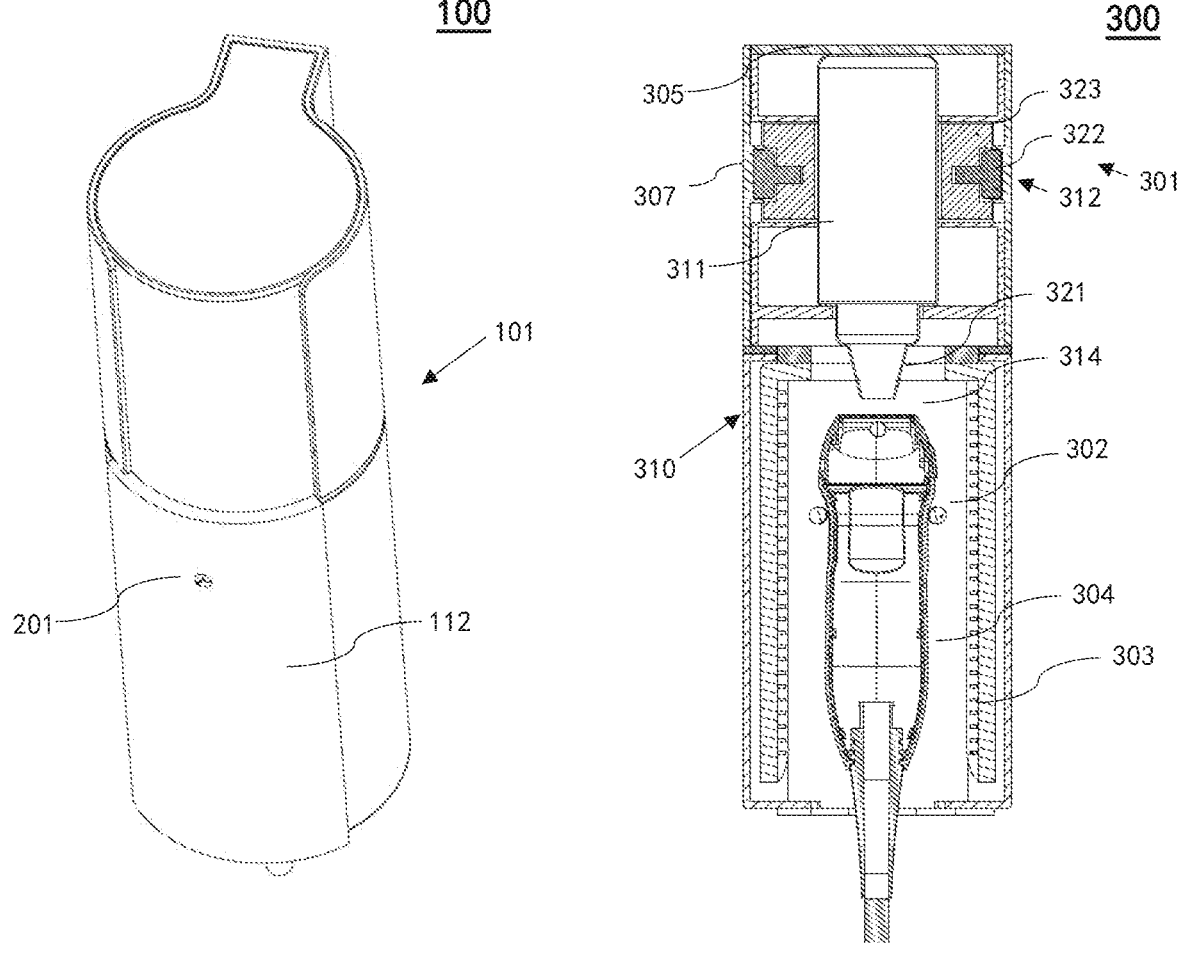
FIG. 2                    FIG. 3

PROBE STERILIZATION DEVICE, PROBE STERILIZATION METHOD, AND ULTRASONIC IMAGING SYSTEM

CROSS-REFERENCE TO RELATED APPLICATION

This application claims priority to Chinese patent application number 202110872476.4, filed on Jul. 30, 2021, the entirety of which is incorporated herein by reference.

TECHNICAL FIELD

The present application relates to the medical field, in particular to a probe sterilization device, a probe sterilization method, and an ultrasonic imaging system including the probe sterilization device.

BACKGROUND

Ultrasonic imaging is a non-destructive and real-time imaging means. Generally, an operator needs to hold an ultrasonic probe to cause the ultrasonic probe to contact a surface of the body of a person to be scanned. The ultrasonic probe transmits an ultrasonic signal to a part that needs to be scanned, and receives an echo signal. Then, an ultrasonic imaging device generates an ultrasonic image on the basis of the received echo signal. For hygiene reasons, the ultrasonic probe needs to be strictly sterilized after each use to avoid cross-infection between different persons to be scanned and even between the person to be scanned and the operator.

However, a sterilization device is generally operated by a user, and when the user operates the sterilization device, contamination between the sterilization device (for example, a sterilization device housing) and a probe that has not been sterilized is also prone to occur. Therefore, it is difficult to avoid the aforementioned cross-infection.

SUMMARY

The aforementioned deficiencies, disadvantages, and problems are solved herein, and these problems and solutions will be understood through reading and understanding of the following description.

The present application discloses a probe sterilization device, comprising: a housing defining a cavity with an opening, wherein the housing includes a cover plate capable of covering the opening, the cavity being capable of accommodating the probe; a cover plate drive, capable of driving, in response to a cover plate drive control signal, the cover plate to move so as to open the opening; a support, arranged in the housing and capable of fixing the probe; an ultraviolet light source, arranged in the housing and capable of being turned on in response to a light source control signal; and a processor, electrically connected to the cover plate drive and capable of sending the cover plate drive control signal to the cover plate drive, and electrically connected to the ultraviolet light source and capable of sending the light source control signal to the ultraviolet light source.

The present application further discloses a probe sterilization method, comprising: sending a cover plate drive control signal to a cover plate drive of a probe sterilization device such that the cover plate drive drives a cover plate of the probe sterilization device to move, so as to open an opening on a housing of the probe sterilization device; sending a light source control signal to an ultraviolet light source of the probe sterilization device, such that the ultraviolet light source is turned on and performs sterilization on the probe placed on a support in the housing; and turning off the ultraviolet light source, and driving the cover plate to move so as to open the opening.

The present application further discloses an ultrasonic imaging system, comprising: a probe, configured to send or receive an ultrasonic signal; a main computer, electrically connected to the probe; and the aforementioned probe sterilization device.

It should be understood that the brief description above is provided to introduce, in simplified form, some concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

FIG. 2 is a perspective view of a probe sterilization device having an opening in a closed state according to some embodiments of the present application;

FIG. 3 is a cross-sectional view of a probe sterilization device according to some embodiments of the present application;

DETAILED DESCRIPTION

Specific implementations of the present application will be described below. It should be noted that in the specific description of these embodiments, for the sake of brevity and conciseness, the present application may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the content disclosed in the present application, some design, manufacture or production changes based on the technical content disclosed in the present disclosure are only common technical means, and should not be construed as insufficient content of the present disclosure.

Unless otherwise defined, the technical or scientific terms used in the claims and the description are as they are usually understood by those of ordinary skill in the art to which the present invention pertains. "First," "second," and similar words used in the present application and the claims do not denote any order, quantity or importance, but are merely intended to distinguish between different constituents. The terms "one" or "a/an" and similar terms do not denote a limitation of quantity, but rather the presence of at least one. The terms "include" or "comprise" and similar terms mean that an ultrasonic transducer or article in front of "include" or "comprise" encompass ultrasonic transducers or articles and their equivalent ultrasonic transducers listed after "include" or "comprise," and do not exclude other ultrasonic transducers or articles. The terms "connect" or "connected" and similar words are not limited to physical or mechanical connections, and are not limited to direct or indirect connections.

Figure 1:
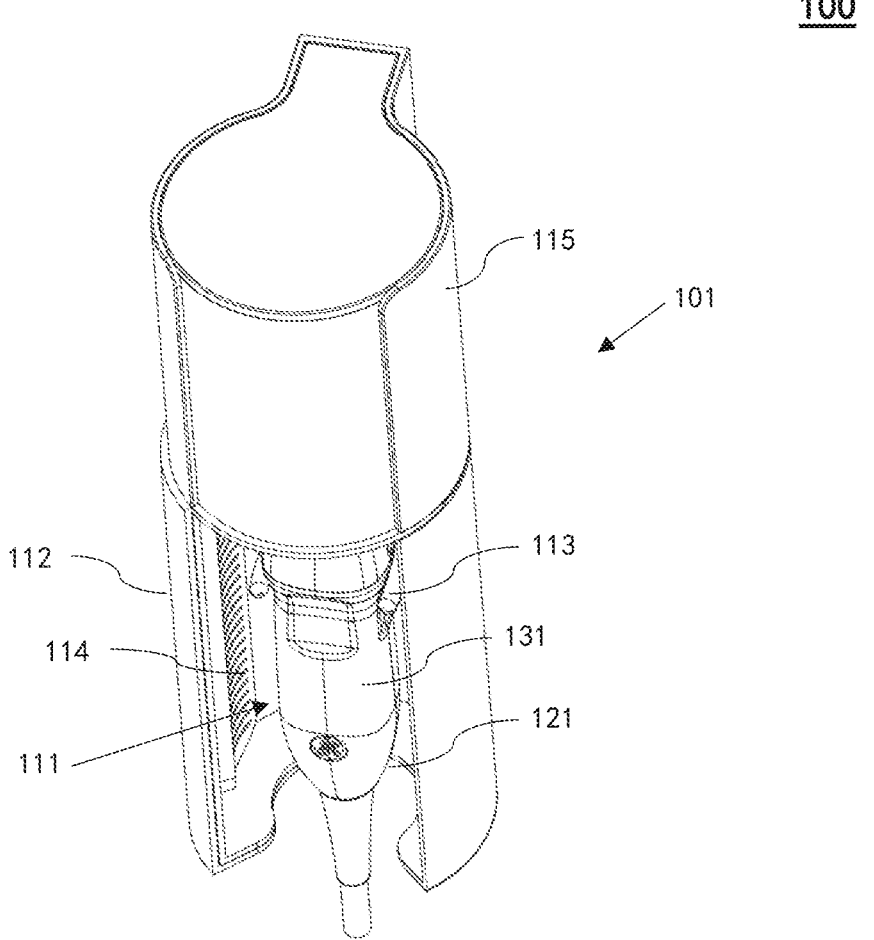
FIG. 1 is a perspective view of a probe sterilization device having an opening in an open state according to some embodiments of the present application.

FIG. 1 is a perspective view of a probe sterilization device 100 having an opening in an open state according to some embodiments of the present application.

As shown in FIG. 1, the probe sterilization device 100 may include a housing 101. The housing 101 defines a cavity 111 with an opening 121. The housing 101 includes a cover plate 112 capable of covering the opening. The cavity 111 is capable of accommodating a probe.

In one example, the cavity 111 may be formed by causing a portion of the housing 101 to form a cylindrical shape. In another example, the cavity 111 may have another shape, such as a cube shape. The cavity 111 is sized to accommodate the probe. Specifically, the cavity 111 can be sized, without occupying a large amount of space, to accommodate probes having different sizes. For example, the cavity 111 is sized to fully accommodate a transducer of the probe and an outer housing of the probe. In this way, the same probe sterilization device 100 is applicable to sterilization of various probes.

FIG. 1 shows a schematic view of the opening 121 in the open state. It can be seen from the figure that the opening 121 may be located on a side wall and a bottom surface of the housing 101. The opening 121 at the side wall allows a user to easily place a probe into the cavity 111 to perform sterilization without contacting the sterilization device 100, thereby avoiding cross contamination. In addition, the opening 121 on the bottom surface allows a cable of the probe to pass therethrough, thereby preventing the cable of the probe from being bent or damaged. It should be understood that other arrangements of the opening 121 are also allowed. Further, by being rotated around the side wall, the cover plate 112 is switched between a state in which the opening 121 is open and a state in which the opening 121 is closed. In the state in which the opening 121 is open, the user can place the probe into the cavity 111 by means of the opening 121. In the state in which the opening 121 is closed, the cover plate 112 can provide protection so as to avoid leakage of sterilization substances (for example, ultraviolet light) and to prevent harm to the user during a sterilization process.

The probe sterilization device 100 may further include a cover plate drive (FIG. 2). The cover plate drive is capable of driving, in response to a cover plate drive control signal, the cover plate to move so as to open the opening. It should be understood that the cover plate drive may be configured in various manners. For example, the cover plate drive may be a motor assembly. The method in which the cover plate drive drives the cover plate may also be any driving method in the art, such as gear-based driving or belt-based driving. The cover plate drive and a specific driving method thereof are exemplarily described below.

Further, the probe sterilization device 100 may further include a support 113 and an ultraviolet light source 114.

The support 113 is arranged in the housing 101 as shown in FIG. 1, and can be configured to fix the probe. Any configuration allowing the support 113 to fix the probe is allowed. For example, in the example of FIG. 1, the support 113 includes a "U"-shaped rod-shaped support. Generally, an end portion of the probe has a large size. In this case, after the user places the probe into the cavity 111, the "U"-shaped rod-shaped support can naturally hold and fix the probe without the need for the user to additionally contact and operate the sterilization device 100. It should be understood that the support 113 may have other shapes, and details will not be described herein.

The ultraviolet light source 114 is arranged in the housing 101, and can be turned on in response to a light source control signal. It should be understood that the ultraviolet light source 114 may be any lamp in the art capable of emitting ultraviolet light. For example, the ultraviolet light source 114 may be a mercury lamp or an LED lamp. After being turned on, the ultraviolet light source 114 can emit ultraviolet light for sterilization. In some embodiments, at least a portion of the ultraviolet light source 114 may be configured to be close to an inner wall of the cavity 111 as shown in FIG. 1. Such configuration can ensure the efficiency of sterilization without affecting the placement of the probe into the cavity 111 performed by the user. The ultraviolet light source 114 may extend in a direction of a main body of the probe, so that the transducer portion and a handle portion of the probe can both be irradiated by ultraviolet light and therefore sterilized. In a preferred embodiment, the inner wall of the cavity 111 may include a material (for example, aluminum foil, silver foil, aluminum or silver coating, and the like) having a good reflection property to ultraviolet light. Such configuration can cause light emitted by the ultraviolet light source 114 to be reflected a plurality of times in the cavity 111, thereby ensuring that all positions on the probe in the cavity 111 can be irradiated by ultraviolet light and therefore fully sterilized.

The probe sterilization device 100 further includes a processor (not shown in the figures). The processor may be configured in various manners. For example, the processor may be arranged in the housing 101. In one embodiment, the processor is arranged in a first portion 115 of the housing 101. The processor may be electrically connected to each electrical component of the probe sterilization device 100 by any means. For example, the electrical connection may be achieved by means of a wire or a printed circuit. In other embodiments, the processor may be electrically connected to the electrical components in a wireless manner. The processor may also be any type of processor in the art. For example, the processor may be a central processing unit (CPU), a microprocessor, a single-chip microcomputer, or the like. Examples are not exhaustively enumerated herein.

Further, the processor is electrically connected to the cover plate drive, and is capable of sending a cover plate drive control signal to the cover plate drive. The cover plate drive is capable of driving, in response to the cover plate drive control signal, the cover plate 112 to move so as to open the opening 121. When open, the opening 121 allows the user to place the probe on the support 113 of the cavity 111. It should be understood that the processor is also capable of sending a cover plate drive control signal to a cover plate drive device so that the cover plate drive drives the cover plate to close the opening 121.

The processor is further electrically connected to the ultraviolet light source 114, and is capable of sending a light source control signal to the ultraviolet light source 114. Further, the ultraviolet light source 114 is turned on in response to the light source control signal. When turned on, the ultraviolet light source 114 can perform sterilization on the probe that has been placed in the cavity 111.

In the configuration according to any aforementioned embodiment, the probe sterilization device 100 according to the present application can fundamentally avoid direct contact between a limb of the user and the probe sterilization device 100, and can achieve a fully automated probe sterilization process. In addition, a portion (for example, the handle of the probe, in one way, contacts the hand of the user, and in another way, may contact the support 113, and can therefore be considered as a medium of indirect contact) of the probe that may result in indirect contact between a limb of the user and the probe sterilization device 100 can be fully sterilized in the cavity without a risk of cross-contamination.

In addition, it should be noted that a power supply method for the various electrical components described above and below may be any power supply method in the art. For example, power supply may be performed by means of a built-in power source of the probe sterilization device 100. In one embodiment, the built-in power source may be a rechargeable lithium battery. Alternatively, the probe sterilization device 100 may not include any power supply, but may be powered by an external power source. Accordingly, the probe sterilization device 100 may include an interface or a circuit for receiving power. Details will not be described herein.

The timing in which the processor sends the cover plate drive control signal to the cover plate drive so as to cause the cover plate to open the opening may be arbitrary. The following is an exemplary description of how the cover plate drive control signal is generated.

Referring to FIG. 2, FIG. 2 shows a perspective view of the probe sterilization device 100 having an opening in a closed state according to some embodiments of the present application. It can be seen from FIG. 2 that when the probe sterilization device 100 is in the closed state, the cover plate 112 covers the opening (not shown in FIG. 2). As described above, in such a configuration, the probe sterilization device 100 can provide a safer sterilization environment, thereby preventing ultraviolet sterilization substances from leaking into an external environment and therefore harming the user.

Further, the probe sterilization device 100 may further include a sensor 201. The sensor 201 is configured to send a sensing signal to the processor upon sensing that the probe is close to the housing 101. The processor sends a cover plate drive control signal to the cover plate drive on the basis of the sensing signal.

Such a configuration allows the probe sterilization device 100 to be automatically opened according to the requirements of the user. The user does not need to contact the probe sterilization device 100 by means of manual operation such as pressing a key, thereby further improving the automation and safety of probe sterilization.

Various types of sensor may be used for the sensor 201. For example, the sensor 201 may be an infrared sensor, a microwave sensor, a camera, or the like. In one embodiment, the sensor 201 may be an infrared sensor or a microwave sensor, and can sense the approach of an object and therefore generate a sensing signal. An approach distance of the object may be freely selected according to the requirements of the user. For example, the approach distance may be from 5 cm to 15 cm. Such a configuration is simple and easy to implement. In another embodiment, the sensor 201 may be a camera. The camera may be configured to capture an image at a certain distance in front of the camera and send the image to the processor such that the processor performs identification. A process of identification may be based on artificial intelligence. For example, an artificial intelligence model stored in the processor may be used to determine whether there is a probe in the image, and only when there is a probe, does the processor determine that this is the time to send a cover plate drive control signal. Further, the processor can further determine, on the basis of the artificial intelligence model, whether an orientation of the probe is correct. For example, the processor determines whether the orientation is consistent with an orientation of the opening. When detecting that there is a probe and that an orientation of the probe is consistent with the orientation of the opening, the processor sends a cover plate drive control signal. In this way, the probability that the user performs misoperation can be further reduced, and misoperation performed by the user on the probe sterilization device 100 when the user holds the probe to perform scanning can be avoided.

The sensor 201 may also be mounted in various positions. In one example, the sensor 201 can be arranged on the cover plate 112. In another example, the sensor 201 can also be arranged in other positions. For example, the sensor 201 can be arranged in any position on the housing 101.

Before performing each ultrasonic scanning, generally, the user needs to apply a couplant onto the ultrasonic transducer of the probe so as to reduce acoustic attenuation of the probe on a surface of tissue to be scanned. The inventors have further found that there is also a risk of cross-contamination in the above process, which is prone to increase the probability that a doctor and a patient become infected. For example, generally, a doctor performing ultrasonic scanning needs to operate a couplant container with one hand and hold the ultrasonic probe with the other hand to apply the couplant. In addition, the couplant container is generally held and used repeatedly over multiple instances of scanning. In this case, an outer surface of the container may not be safe. The couplant container and the transducer of the probe may even contact each other and thus result in contamination.

In order to at least solve the problem found by the inventors, the probe sterilization device according to some embodiments of the present application may further include a couplant releasing assembly. The couplant releasing assembly may include a couplant container and a release drive. The couplant container is arranged above the support in the housing, and the couplant container accommodates the couplant. The release drive acts on the couplant container in response to a release signal so as to release the couplant from the couplant container.

Such a configuration can achieve fully automatic couplant application and avoid manual operation of the user, thereby avoiding a risk of contamination and cross-infection. In addition, since the transducer portion of the ultrasonic probe is exposed to a sterilization environment such as ultraviolet light, correspondingly, the couplant applied to the probe will also be sterilized, thereby further reducing the risk. According to the aforementioned embodiments, the probe sterilization device according to the present application can achieve closed-loop sterilization of the probe throughout an entire service period, thereby greatly increasing the probability that the user and the person to be scanned become infected.

Automatic control of the couplant releasing assembly may be achieved by the processor described in any embodiment.

For example, the processor may be electrically connected to the release drive, and be capable of sending a release signal to the release drive. In addition, after a predetermined release condition is met, the processor can also control the release drive to stop acting on the couplant container so as to end couplant releasing.

It should be understood that various shapes and materials may be used for the couplant container. In some embodiments, the couplant container may be made of a material prone to be deformed or broken under external force, such as plastic, so that the couplant in the container can be released under the action of the release drive. The release drive may also be configured in various manners. For example, the release drive may be an electromechanical drive device or an electromagnetic drive device. On the basis of the teaching of the present disclosure, those skilled in the art could autonomously perform selection. The following is a specific exemplary description of the configuration of the couplant releasing assembly.

FIG. 3 shows a cross-sectional view of a probe sterilization device 300 according to some embodiments of the present application. In addition to a support 302 and an ultraviolet emitting device 303 similar to those described above, the probe sterilization device 300 further includes a couplant releasing assembly 301. The couplant releasing assembly may include a couplant container 311 and a release drive 312. The couplant container 311 is arranged above the support 302 in the housing 310. In some embodiments, the couplant container 311 may be arranged in a first portion 307 of the housing of the probe sterilization device 300. The couplant container 311 has a container opening 321. The couplant container 311 being arranged above the support 302 in the housing means that the container opening 321 is located above the support 302. In this way, when a transducer of a probe 303 faces upwards and is fixed on the support 302, a couplant flows out from the container opening 321 after being operated, and drops directly onto and is applied to the transducer 314 of the probe 304. Further, the release drive 312 may include an electric drive 322 and a pressing block 323. The pressing block 323 is connected to the couplant container 311, and is driven by the electric drive 322 to press the couplant container 311.

In some embodiments, the electric drive 322 may be a drive motor, and the drive motor may be screwed to the pressing block 323 by means of an output shaft. After receiving a release signal, the drive motor rotates so as to drive the pressing block 323 to move and act on the couplant container 311. The pressure of the pressing block 323 deforms the couplant container 311, so that the couplant is released from the couplant container 311 and applied to the transducer 314 of the probe 304. It should be understood that the drive motor can also stop driving or reversely rotate the output shaft of the motor according to a signal, so as to stop pressing the couplant container 311. The above processes can all be controlled by the processor disclosed herein.

In addition, the housing may further include a detachable top plate 305. When the couplant in the couplant container is used up, the couplant can be replaced by opening the top plate.

Figure 4:
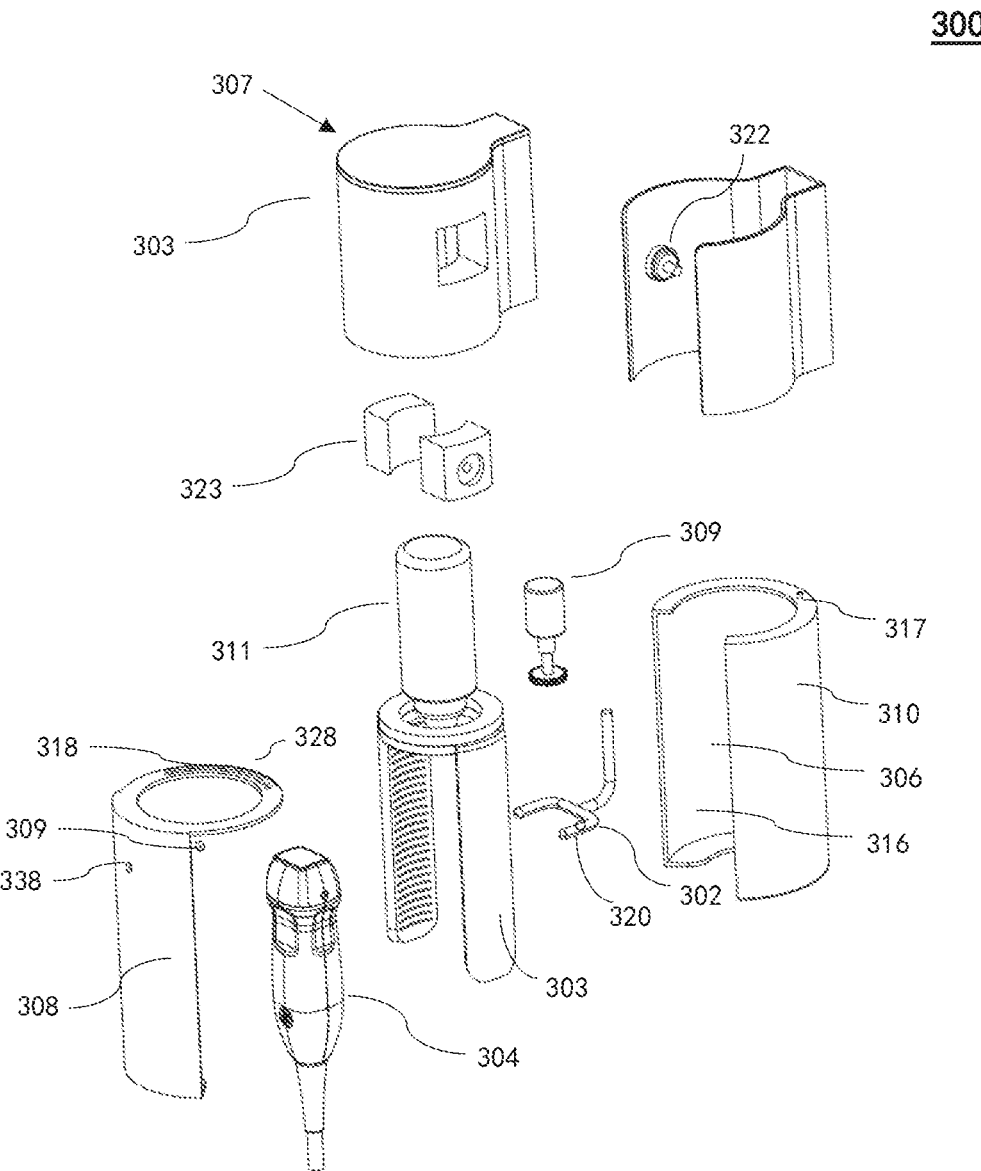
FIG. 4 is a perspective exploded view of the probe sterilization device shown in FIG. 3.

Referring to FIG. 4, the probe sterilization device 300 according to the present application is further described. FIG. 4 shows a perspective exploded view of the probe sterilization device 300 shown in FIG. 3 according to some embodiments of the present application.

The housing 310 of the probe sterilization device 300 may define a cavity 306 with an opening 316 and a first portion 307 arranged on the cavity 306. Similar to those described above, the opening 316 of the cavity 306 can be covered by a cover plate 308.

The cover plate 308 may include a portion covering the opening 316 and a portion for connection to the housing 310. For example, the cover plate 308 may include an annular structure arranged on a top portion so as to be connected to the housing. The annular structure has a hollow slide rail 318. In addition, a stopper 317 may be provided in a corresponding position on the cavity 306 of the housing 310, and the stopper 317 is mounted in the hollow slide rail 318. In this way, the cover plate 308 can rotate around an outer portion of the cavity 306, and can be position-limited by means of the stopper 317.

Further, the probe sterilization device 300 may further include a cover plate drive 309. The cover plate drive 309 is capable of driving, in response to a cover plate drive control signal, the cover plate 308 to move so as to open the opening 316. In some embodiments, the cover plate drive 309 may include a cover plate drive motor. A gear structure is mounted on an output shaft of the drive motor. Correspondingly, the exterior of the annular structure of the cover plate 308 is further provided with a gear 328. The cover plate 308 and the cover plate drive motor mesh with and are connected to each other by means of two sets of gears, so that the cover plate drive 309 can drive the cover plate 308.

The ultraviolet light source 303 may be configured to be two opposite ultraviolet light sources so as to fully and comprehensively sterilize the probe. A longitudinal length thereof can extend to a bottom portion of the entire probe, thereby further improving the efficiency of probe sterilization.

The cover plate 308 may define an opening 338 for accommodating a sensor 309. The specific configuration and function of the sensor 309 may be any of those described in the present disclosure, and details will not be described herein.

An inner surface of the pressing block 323 may be configured to match the shape of an outer surface of the couplant container 311 so as to provide a stable and uniform pressing force. For example, the inner surface of the pressing block 323 may be configured to have a curved shape matching the cylindrical couplant container 311. FIG. 4 shows an embodiment in which two pressing blocks are provided. However, it should be understood that the number of pressing blocks can be arbitrary.

In addition, the probe sterilization device 300 may further include a probe position sensor 320. The probe position sensor 320 is mounted on the support, and is electrically connected to a processor (not shown). The probe position sensor 320 is configured to send a probe position sensing signal to the processor when the probe 304 is fixed to the support 302.

Such a configuration can ensure that after the probe is mounted in place, the processor can learn, without any additional operation to be performed by the user, that the probe is mounted in place, so that the next operation, such as closing the opening, turning on the ultraviolet light source, or applying the couplant, can be performed. This procedure further increases the automation and safety of the sterilization device.

The probe position sensor 320 may be configured in various manners. For example, the probe position sensor 320 may be a switch that can be pressed. After the probe is mounted on the support, the probe presses the switch to turn on a loop, such that a probe position sensing signal is generated and sent to the processor. In addition, the probe position sensor may also be a weight sensor. After the probe is mounted in place, a load on the support is increased. Therefore, a probe position sensing signal can also be generated and sent to the processor. Examples are not exhaustively enumerated herein.

In some embodiments, the ultraviolet light source 303 may be fixed in the cavity. In some other embodiments, the ultraviolet light source may be configured to be mobile. The ultraviolet light source can be driven by means of an ultraviolet light source drive (not shown). Specifically, the ultraviolet light source drive may be connected to the ultraviolet light source 303, and is capable of driving, in response to a light source driving signal, the ultraviolet light source 303 to move around the probe. For configuration of the ultraviolet light source drive, please refer to the cover plate drive shown in FIG. 4. For example, the ultraviolet light source drive may include a drive motor and a gear (or a thread) connected to the drive motor. Correspondingly, the ultraviolet light source 303 may have a gear structure similar to the gear structure of the cover plate shown in FIG. 4. In this way, the ultraviolet light source can be driven by the motor to move around the probe. In addition, other driving methods are also allowed. Examples are not exhaustively enumerated herein.

Such a configuration enables the ultraviolet light source to more automatically and fully sterilize the probe.

It should be understood that the light source driving signal may come from the processor. Specifically, the processor may be electrically connected to the ultraviolet light source drive, and can send the light source driving signal to the ultraviolet light source drive. The timing for sending the light source driving signal may be a fixed time period after the cover plate closes the opening. For example, the timing may be ten seconds after the cover plate closes the opening. Alternatively, optionally, the light source driving signal may be sent after the probe position sensor has sent a probe position signal.

Figure 5:
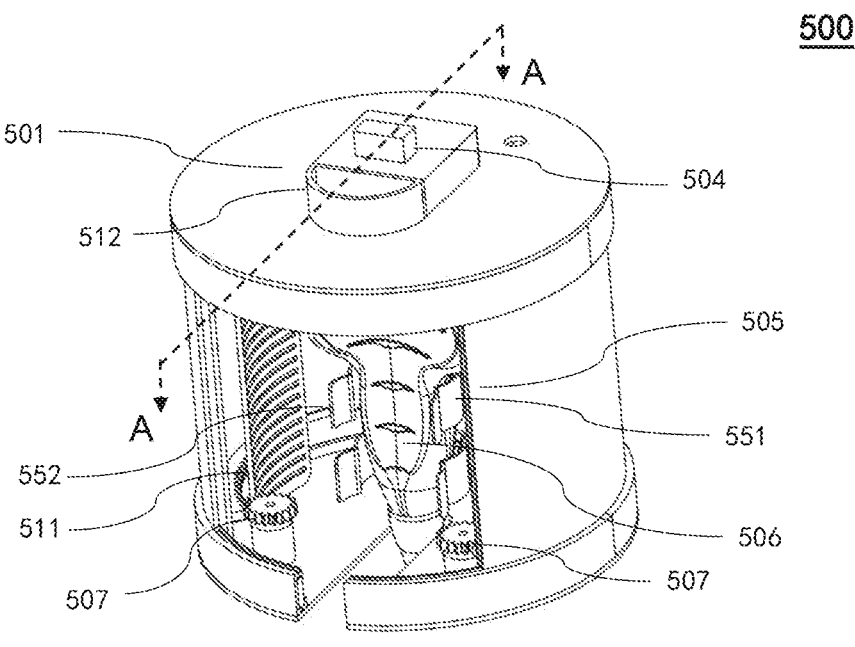
FIG. 5 is a perspective view of a probe sterilization device according to some other embodiments of the present application.
Figure 6:
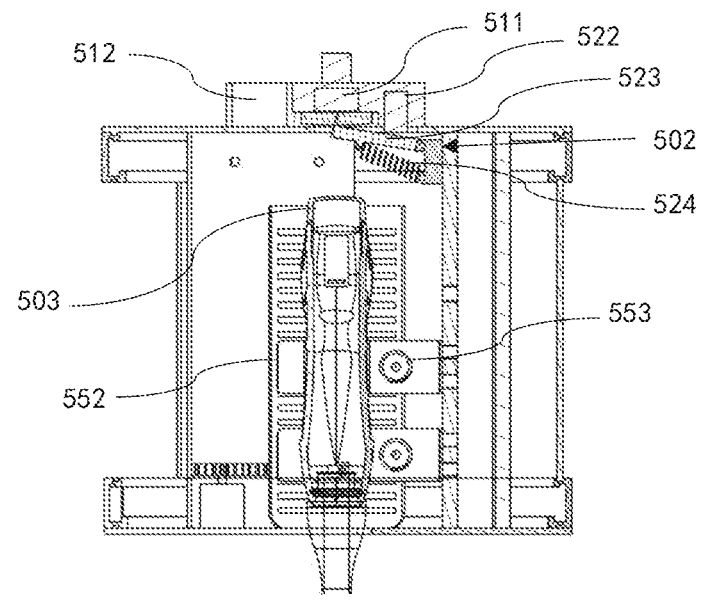
FIG. 6 is a cross-sectional view of the probe sterilization device of FIG. 5 taken along line A-A.

Referring to FIG. 5 and FIG. 6, said drawings show a configuration of a probe sterilization device 500 according to some other embodiments of the present application. FIG. 5 shows a perspective view of the probe sterilization device 500 according to some other embodiments of the present application. FIG. 6 shows a cross-sectional view of the probe sterilization device 500 of FIG. 5 taken along line A-A.

In this alternative embodiment, an alternative implementation of each component is provided. For example, a couplant container 501 includes a couplant capsule 511 and a capsule support 512 for accommodating the capsule. In addition, a release drive 502 may include an electric drive 522 and a needle 523 connected to the electric drive. The needle 523 is driven by the electric drive 522 to pierce the couplant capsule 511. Further, a couplant accommodated in the couplant capsule 511 flows out and is released onto an ultrasonic transducer 503 therebelow, so that the couplant is applied.

In this way, the couplant capsule 511 and the capsule support 512 can be configured for single use. For example, the couplant capsule 511 and the capsule support 512 are discarded after single use to avoid secondary contamination. In addition, it is also possible to reuse the capsule support 512 and to replace merely the couplant capsule 511 after each use.

Continue to refer to FIG. 6. The release drive 502 may include the electric drive 522 and the needle 523 connected to the electric drive. In one embodiment, the electric drive 522 may be an electromagnet. In addition, the needle 523 may be made of a material that can be attracted by an electromagnet, such as iron. It should be understood that the two are connected to each other by means of a magnetic field. In a non-operating state of the electromagnet, the needle hangs down due to gravity, and does not contact the couplant capsule 511. After receiving a signal from a processor and being energized, the electromagnet attracts the needle 523. The needle 523 rotates upwards to pierce the couplant capsule 511 as shown in FIG. 6. When the processor performs controlling to stop energizing the electromagnet, the needle 523 can hang down under gravity so as to stop acting on the couplant capsule 511. In an alternative embodiment, in order to ensure that the needle 523 is not stuck in the couplant capsule 511, the release drive 502 may further include a spring 524 as shown in FIG. 6. The spring 524 is connected to the needle 523 so as to provide resilience force for the needle. It should be understood that the connection between the electric drive 522 and the needle 523 and driving methods therefor may be in other forms. For example, driving may be performed by means of a motor.

In addition, in some embodiments, a capsule sensor 504 may further be included, and is configured to sense whether the couplant capsule 511 is mounted in place. A sensing result may also be sent to the processor. Therefore, if the couplant capsule 511 is not mounted, the processor can ascertain the situation so as to provide a prompt in the form of sound or a light alarm signal, or the processor does not perform subsequent operation accordingly.

Referring to FIG. 5 and FIG. 6, said drawings further provide alternative embodiments of the various components described above. A plurality of supports 505 may be provided. For example, two supports 505 may be provided. In addition, the support 505 may have a sheet shape. In addition, each support 505 may include a first portion 551 and a second portion 552. The two portions may be movably connected to each other, and a support spring 553 may be provided at the connection location. Such a configuration can improve the firmness of probe fixation. In addition, the support spring 553 can ensure that an opening of the support is adjustable so as to adapt to probes 506 having different sizes. In addition, two cover plate drive devices 507 may be provided, and the positions thereof may be located on a bottom portion of a cavity.

It should be understood that on the basis of the teaching of the present disclosure, all of the aforementioned implementations are interchangeable or replaceable relative to each other.

Figure 7:
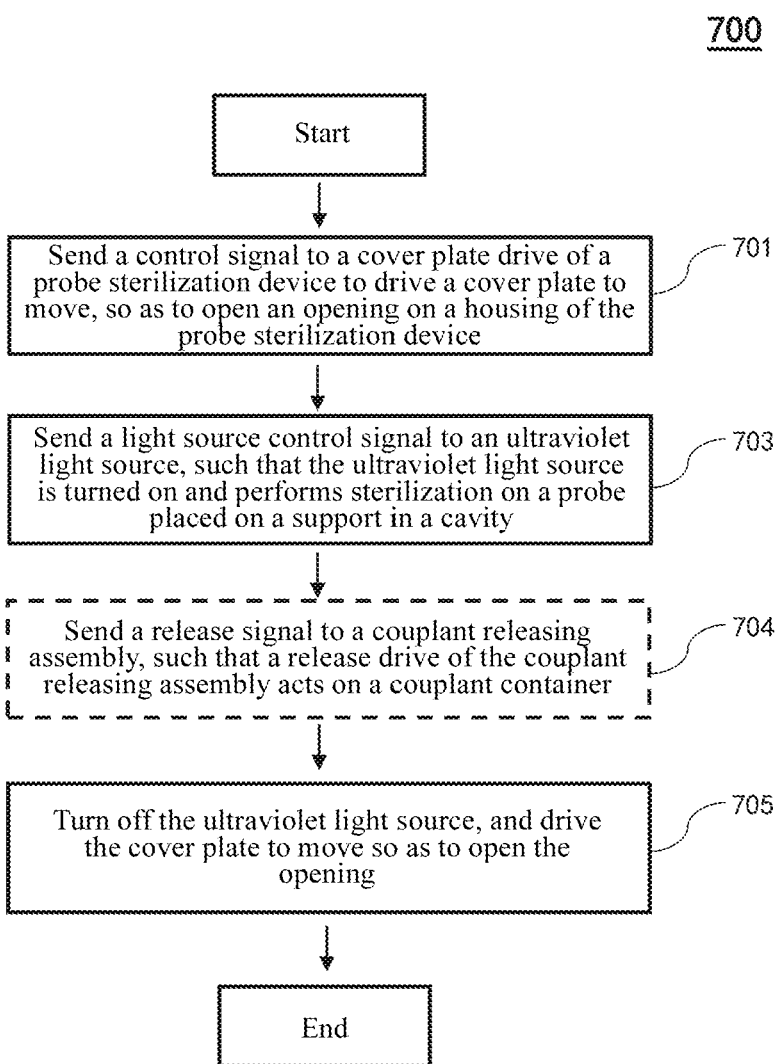
FIG. 7 is a flowchart of a probe sterilization method according to some embodiments of the present application.

The present application further discloses a probe sterilization method. FIG. 7 shows a flowchart of a probe sterilization method 700 according to some embodiments of the present application. The probe sterilization method can be automatically implemented by means of the probe sterilization device according to any one of the embodiments herein.

In step 701, a cover plate drive control signal is sent to a cover plate drive of a probe sterilization device such that the cover plate drive drives a cover plate to move, so as to open an opening on a housing of the probe sterilization device.

This step may be performed by a processor. As described above, the processor may be a portion of the probe sterilization device. The timing for sending the control signal may be based on an instruction of a user, such as a voice instruction. Alternatively, as described above, the timing for sending the control signal may be based on a sensing signal received by the processor from a sensor upon sensing that a probe is close to the housing of the probe sterilization device.

This step allows the user to open the cover plate without contacting the cover plate, so as to place the probe in a cavity to perform a subsequent sterilization step.

In step 703, a light source control signal is sent to an ultraviolet light source of the probe sterilization device, such that the ultraviolet light source is turned on and performs sterilization on the probe placed in the cavity.

This step may be performed by the processor. In some embodiments, the timing for sending the light source control signal may be a certain fixed time period after step 701, for example, within 20 seconds. In this way, the processor considers by default that the user has enough time to complete the operation of probe fixation. In some other embodiments, the timing for sending the light source control signal may be based on the fact that the aforementioned probe position sensor senses that the probe is mounted in place and sends a probe position sensing signal to the processor. Such a configuration allows the ultraviolet light source to be turned on more accurately.

In step 705, the ultraviolet light source is turned off, and the cover plate is driven to move so as to open the opening.

This step may be performed by the processor. The process of turning on the ultraviolet light source is described in detail above, and the process of turning off the ultraviolet light source may be similar to the process of turning on the ultraviolet light source, and details will not be described herein again. In one embodiment, the processor drives the cover plate to open the opening after the ultraviolet light source is turned off so as to avoid an adverse effect caused by a ray on the user. The timing for turning off the ultraviolet light source may be within a fixed time period after the ultraviolet light source is turned on in the above step, for example, two to five minutes. Alternatively, the ultraviolet light source may be turned off automatically on the basis that the sensor senses that the user is approaching. Such a configuration allows the probe to be removed immediately according to the requirements of the user, and is therefore more flexible.

When open, the opening allows the user to remove the sterilized probe, thereby forming a fully automatic and non-contact closed-loop probe sterilization process.

In a non-limiting embodiment, the method may further include step 704. In step 704, a release signal is sent to a couplant releasing assembly of the probe sterilization device, such that a release drive of the couplant releasing assembly acts on a couplant container.

This step may be performed by the processor. This step may be performed before step 705, so that a couplant is applied to an ultrasonic transducer before the user removes the probe. On the one hand, this configuration saves time for the user, and on the other hand, the couplant can also be sterilized to further improve safety.

The probe sterilization device disclosed in the present application can be applied to various application scenarios. The probe sterilization device can serve as a portion of an ultrasonic imaging system. For example, the probe sterilization device can be fixed on an ultrasonic imaging device in any manner, or on a wall or a support close to the ultrasonic imaging device. In addition, the fixing may be performed by any means, for example, by means of an adhesive or a screw or by any other means.

Figure 8:
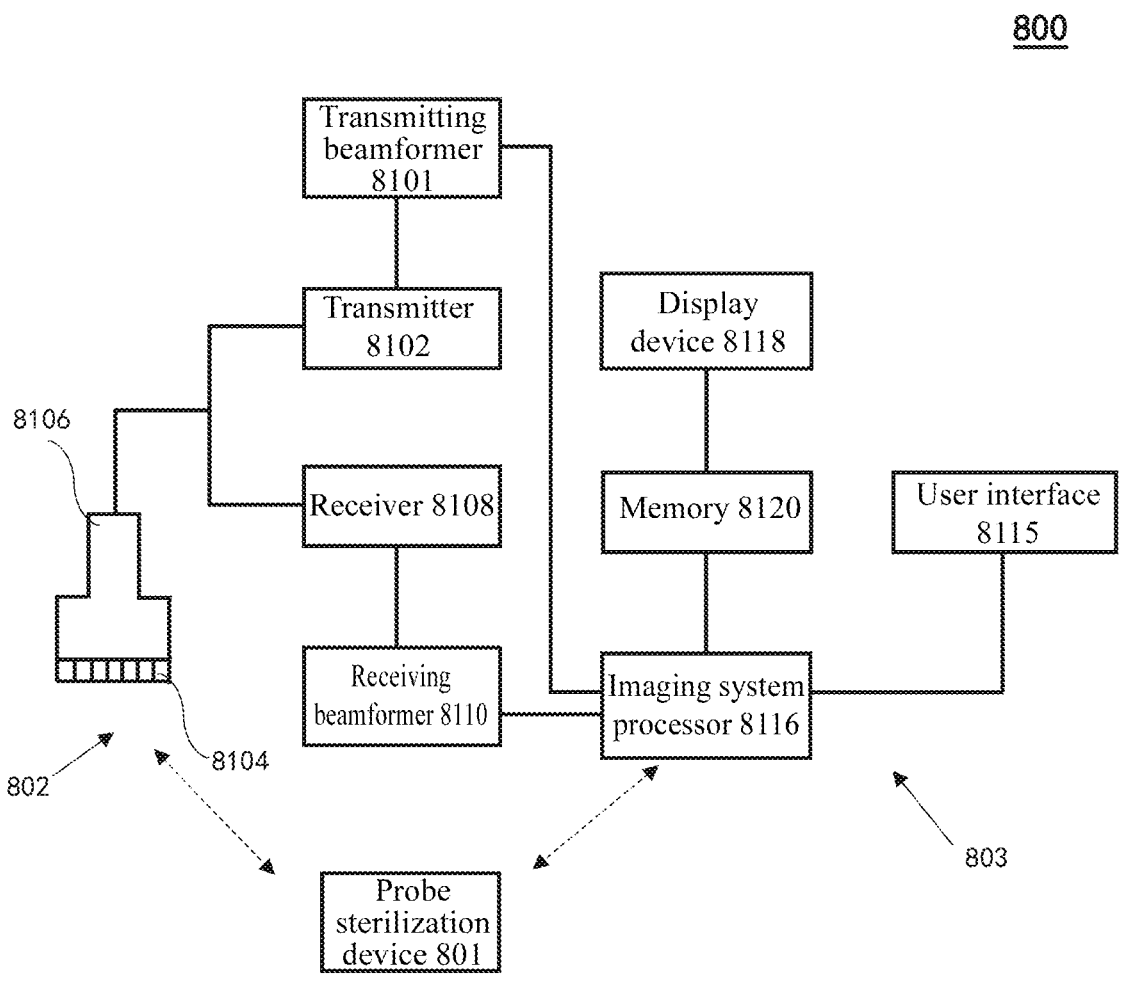
FIG. 8 is a schematic view of an ultrasonic imaging system including a probe sterilization device according to some embodiments of the present application.

FIG. 8 provides a schematic view of an ultrasonic imaging system 800 including a probe sterilization device 801. The ultrasonic imaging device 800 includes: a probe 802 configured to send or receive an ultrasonic signal; a main computer 803 electrically connected to the probe 802; and the probe sterilization device 801 described in any one of the above embodiments. That is, the probe sterilization device 801 may be the probe sterilization device disclosed in any one of the embodiments of the present disclosure.

Components of the ultrasonic imaging system 800 are exemplarily described below.

The ultrasonic imaging system 800 includes a transmitting beamformer 8101 and a transmitter 8102, and the two drive an ultrasonic transducer 8104 in the probe 802 to transmit ultrasonic pulse signals into the body (not shown). According to various embodiments, the probe 802 may be any type of probe including a linear probe, a curved array probe, a 1.25 D array probe, a 1.5 D array probe, a 1.75 D array probe, or a 2 D array probe. According to other embodiments, the probe 802 may also be a mechanical probe, for example, a mechanical 4 D probe or a hybrid probe. The probe 802 may be configured to acquire 4 D ultrasonic data, and the 4 D ultrasonic data includes information on how the volume changes over time. Each volume may include a plurality of 2 D images or slices. The ultrasonic pulse signals are backscattered from structures in the body (for example, blood cells or muscle tissue) to produce echoes, and the echoes return to the ultrasonic transducer 8104. The echoes are converted by the ultrasonic transducer 8104 into electrical signals or ultrasonic data, and the electrical signals are received by a receiver 8108. The electrical signals representing the received echoes pass through a receiving beamformer 8110 that outputs ultrasonic data. According to some embodiments, the probe 802 may include an electronic circuit to perform all of or part of transmitting beamforming and/or receiving beamforming. For example, all of or part of the transmitting beamformer 8101, the transmitter 8102, the receiver 8108, and the receiving beamformer 8110 may be located in the probe 802, such as in an outer housing 8106 of the probe 802. The above components can be considered as a portion of the probe. It should be understood that the components may also be arranged in the main computer 803. The term "scan" or "scanning" may also be used in the present disclosure to refer to acquiring data through the process of transmitting and receiving ultrasonic signals. The terms "data" and "ultrasonic data" may be used in the present disclosure to refer to one or a plurality of datasets acquired using the ultrasonic imaging system.

The main computer 803 of the ultrasonic imaging system 800 may include various components including a user interface 8115, an imaging system processor 8116, a memory 8120, and a display device 8118.

A user interface 8115 may be configured to control operation of the ultrasonic imaging system 800. The user interface may be configured to control input of patient data, or select various modes, operations, parameters, and so on. The user interface 8115 may include one or a plurality of user input devices, for example, a keyboard, hard keys, a touch pad, a touch screen, a trackball, a rotary control, a trackball, soft keys, or any other user input device.

The ultrasonic imaging system 800 further includes an imaging system processor 8116, and the imaging system processor 8116 controls the transmitting beamformer 8101, the transmitter 8102, the receiver 8108, and the receiving beamformer 8110. According to various embodiments, the receiving beamformer 8110 may be a conventional hardware beamformer or software beamformer. If the receiving beamformer 8110 is a software beamformer, then the receiving beamformer 8110 may include one or a plurality of the following components: a graphics processing unit (GPU), a microprocessor, a central processing unit (CPU), a digital signal processor (DSP), or any other type of processor capable of performing logical operations. The beamformer 110 may be configured to implement conventional beam-forming techniques and techniques such as retrospective transmit beam formation (RTB).

The imaging system processor 8116 is in electronic communication with the probe 802. The imaging system processor 8116 may control the probe 802 to acquire ultrasonic data. The imaging system processor 8116 controls which ultrasonic transducer 104 is activated and the shape of a beam transmitted from the probe 802. The imaging system processor 8116 is further in electronic communication with a display device 8118. The imaging system processor 8116 may process the ultrasonic data into an image and display the same on the display device 8118. For the purpose of the present disclosure, the term "electronic communication" may be defined to include wired connection and wireless connection. According to an embodiment, the imaging system processor 8116 may include a central processing unit (CPU). According to other embodiments, the imaging system processor 8116 may include other electronic components capable of performing processing functions, for example, a digital signal processor, a field-programmable gate array (FPGA), a graphics processing unit (GPU), or any other type of processor. According to other embodiments, the imaging system processor 8116 may include a plurality of electronic components capable of performing processing functions. For example, the imaging system processor 8116 may include two or more electronic components selected from a list including the following electronic components: a central processing unit (CPU), a digital signal processor (DSP), a field-programmable gate array (FPGA), and a graphics processing unit (GPU). According to another embodiment, the imaging system processor 8116 may include a complex demodulator (not shown). The complex demodulator performs demodulation to acquire RF data, and generates raw data. In another embodiment, the demodulation may be performed earlier in the processing chain. The imaging system processor 8116 may be adapted to perform one or a plurality of processing operations on data according to a plurality of selectable ultrasound modalities. As echo signals are received, data may be processed in real time in a scanning stage. For the purpose of the present disclosure, the term "real time" is defined to include a process that is performed without any intentional delay. The real-time frame or volume rate may vary on the basis of the site where data is acquired or the size of the volume and specific parameters used in the acquisition process. The data may be temporarily stored in a buffer (not shown) in the scanning stage, and processed in a less real-time manner in live or offline operations.

According to an embodiment, the ultrasonic imaging system 800 may continuously acquire ultrasonic data at a frame rate of, for example, 10 Hz to 30 Hz. An image generated from the data may be refreshed at a similar frame rate. Data may be acquired and displayed at different rates in other embodiments. For example, depending on the size of the volume and potential applications, ultrasonic data may be acquired at a frame rate of less than 10 Hz or greater than 30 Hz in some embodiments. For example, many applications involve acquiring ultrasonic data at a frame rate of 50 Hz. The memory 8120 is included therein to store processing frames for acquiring data. In an exemplary embodiment, the memory 8120 has sufficient capacity to store ultrasonic data frames acquired over a period of time that are at least a few seconds long. The data frames are stored in a manner that facilitates retrieval according to the order or time of acquisition thereof. The memory 8120 may include any known data storage medium.

The probe 802 needs to be sterilized during a scanning interval. In this case, the probe 802 can be connected to and sterilized by the probe sterilization device 801. The fully automatic sterilization process ensures the safety of the user and the person to be scanned.

In addition, a processor of the probe sterilization device 801 may be the imaging system processor 8116 of the ultrasonic imaging system 800. Such a configuration facilitates integration between the ultrasonic imaging system 800 and the probe sterilization device 801, and ultrasonic imaging and sterilization of the probe 802 can be uniformly controlled by the same processor. Such a configuration can be implemented by connecting the ultrasonic imaging device 800 by means of an interface arranged on the probe sterilization device 801 and a cable. In addition, it is also possible to use the cable to supply power to the probe sterilization device 801 so as to achieve a higher degree of integration. In another embodiment, the aforementioned integrated configuration is not necessary, and the probe sterilization device 801 may also have an independent processor and battery so that the mounting position is more flexible.

The purpose of providing the above specific embodiments is to allow the content disclosed in the present application to be understood more thoroughly and comprehensively, but the present application is not limited to these specific embodiments. Those skilled in the art should understand that various modifications, equivalent replacements, and changes can also be made to the present application and should be included in the scope of protection of the present application as long as these changes do not depart from the spirit of the present application.

The invention claimed is:

1. A sterilization device for an ultrasonic probe, comprising:

a housing defining a cavity with an opening, wherein the housing comprises a cover plate capable of covering the opening, the cavity being capable of accommodating the ultrasonic probe;

a cover plate drive, capable of driving, in response to a cover plate drive control signal, the cover plate to move so as to open the opening;

a support, arranged in the housing and capable of fixing the ultrasonic probe;

an ultraviolet light source, arranged in the housing, and capable of being turned on in response to a light source control signal;

a processor, electrically connected to the cover plate drive and capable of sending the cover plate drive control signal to the cover plate drive, and electrically connected to the ultraviolet light source and capable of sending the light source control signal to the ultraviolet light source; and a couplant releasing assembly, comprising a couplant container and a release drive, the couplant container being arranged above and facing the support in the housing, the couplant container accommodating a couplant, and the release drive acting on the couplant container in response to a release signal so as to release the couplant from the couplant container onto a transducer of the ultrasonic probe while the transducer of the ultrasonic probe faces the couplant releasing assembly and is fixed to the support, wherein the couplant container comprises a couplant capsule and a capsule support for accommodating the capsule, and the release drive comprises an electric drive and a needle connected to the electric drive, the needle being driven by the electric drive to pierce the couplant capsule.

2. The sterilization device according to claim 1, wherein the sterilization device further comprises:
    a sensor, configured to send a sensing signal to the processor upon sensing that the ultrasonic probe is close to the housing, such that the processor sends the cover plate drive control signal to the cover plate drive based on the sensing signal.

3. The sterilization device according to claim 1, wherein the sterilization device further comprises:
    a probe position sensor, mounted on the support, electrically connected to the processor, and configured to send a probe position sensing signal to the processor when the probe is fixed to the support.

4. The sterilization device according to claim 1, wherein the cavity is sized to fully accommodate the transducer of the probe and an outer housing of the probe.

5. The sterilization device according to claim 1, wherein the processor is electrically connected to the release drive, and is capable of sending the release signal to the release drive.

6. The sterilization device according to claim 1, wherein the couplant container has a downward opening, the release drive comprises an electric drive and a pressing block, and the pressing block is connected to the couplant container and is driven by the electric drive to press the couplant container.

7. The sterilization device according to claim 1, wherein the sterilization device further comprises:
    an ultraviolet light source drive, connected to the ultraviolet light source and capable of driving, in response to a light source driving signal, the ultraviolet light source to move around the ultrasonic probe.

8. The sterilization device according to claim 7, wherein the processor is electrically connected to the ultraviolet light source drive, and is capable of sending the light source driving signal to the ultraviolet light source drive.

9. The sterilization device according to claim 1, wherein the support is U-shaped.

10. An ultrasonic imaging system, comprising:
    an ultrasonic probe, configured to send or receive an ultrasonic signal;
    a main computer, electrically connected to the ultrasonic probe; and
    a sterilization device, comprising:
    a housing defining a cavity with an opening, wherein the housing comprises a cover plate capable of covering the opening, the cavity being capable of accommodating the ultrasonic probe;
    a cover plate drive, capable of driving, in response to a cover plate drive control signal, the cover plate to move so as to open the opening;
    a support, arranged in the housing and capable of fixing the ultrasonic probe;

an ultraviolet light source, arranged in the housing, and capable of being turned on in response to a light source control signal; and
    a processor, electrically connected to the cover plate drive and capable of sending the cover plate drive control signal to the cover plate drive, and electrically connected to the ultraviolet light source and capable of sending the light source control signal to the ultraviolet light source,
    wherein the sterilization device further comprises a couplant releasing assembly, the couplant releasing assembly comprises a couplant container and a release drive, the couplant container is arranged above and faces the support in the housing and accommodates a couplant, and the release drive acts on the couplant container in response to a release signal so as to release the couplant from the couplant container onto a transducer of the ultrasonic probe while the transducer of the ultrasonic probe faces the couplant releasing assembly and is fixed to the support,
    wherein the couplant container comprises a couplant capsule and a capsule support for accommodating the capsule, and the release drive comprises an electric drive and a needle connected to the electric drive, the needle being driven by the electric drive to pierce the couplant capsule.

11. The ultrasonic imaging system according to claim 10, wherein the sterilization device further comprises:
    a sensor, configured to send a sensing signal to the processor upon sensing that the ultrasonic probe is close to the housing, such that the processor sends the cover plate drive control signal to the cover plate drive based on the sensing signal.

12. The ultrasonic imaging system according to claim 10, wherein the sterilization device further comprises:
    a probe position sensor, mounted on the support, electrically connected to the processor, and configured to send a probe position sensing signal to the processor when the ultrasonic probe is fixed to the support.

13. The ultrasonic imaging system according to claim 10, wherein the couplant container has a downward opening, the release drive comprises an electric drive and a pressing block, and the pressing block is connected to the couplant container and is driven by the electric drive to press the couplant container.

14. The ultrasonic imaging system according to claim 10, wherein the sterilization device further comprises:
    an ultraviolet light source drive, connected to the ultraviolet light source and capable of driving, in response to a light source driving signal, the ultraviolet light source to move around the ultrasonic probe.

15. The ultrasonic imaging system according to claim 14, wherein the processor is electrically connected to the ultraviolet light source drive, and is capable of sending the light source driving signal to the ultraviolet light source drive.

* * * * *